US006320375B1

(12) United States Patent
Cotton et al.

(10) Patent No.: US 6,320,375 B1
(45) Date of Patent: Nov. 20, 2001

(54) METHOD FOR DETECTION OF RARE EARTH METAL OXIDE INCLUSIONS IN TITANIUM AND OTHER NON-MAGNETIC OR METAL ALLOY CASTINGS

(75) Inventors: James D. Cotton; Darryl F. Garrigus, both of Issaquah, WA (US)

(73) Assignee: The Boeing Company, Seattle, WA (US)

( * ) Notice: Subject to any disclaimer, the term of this patent is extended or adjusted under 35 U.S.C. 154(b) by 0 days.

(21) Appl. No.: 09/399,917

(22) Filed: Sep. 21, 1999

(51) Int. Cl.[7] .......................... G01R 33/12; G01R 33/07; G01R 27/82
(52) U.S. Cl. ......................... 324/238; 324/251; 324/235
(58) Field of Search .................. 324/207.13, 207.22, 324/228, 238, 239, 251, 240, 235

(56) References Cited

U.S. PATENT DOCUMENTS

| 3,065,412 | 11/1962 | Rosenthal ............................... 324/41 |
| 4,518,919 | 5/1985 | Ishida .................................... 324/228 |
| 4,719,421 | 1/1988 | Kerr ...................................... 324/233 |
| 4,814,734 | 3/1989 | Moran .................................... 336/84 |
| 4,902,997 | 2/1990 | Moran .................................... 336/84 |
| 4,943,770 | 7/1990 | Ashley-Rollman et al. ... 324/207.17 |
| 5,105,151 | 4/1992 | Takahashi et al. ................... 324/235 |
| 5,128,613 | 7/1992 | Takahashi ............................. 324/235 |
| 5,432,444 | 7/1995 | Yasohama et al. ................... 324/240 |
| 5,589,772 | 12/1996 | Kugai ................................... 324/240 |
| 5,975,188 | * 11/1999 | Lassow et al. ...................... 164/76.1 |

* cited by examiner

Primary Examiner—Benjamin R. Fuller
Assistant Examiner—Henry S. Andersen
(74) Attorney, Agent, or Firm—Conrad O. Gardner

(57) ABSTRACT

A method and apparatus for detection of rare earth metal oxide inclusions in non-magnetic metal. The method utilizes a D.C. magnetic search field coupled with a magnetic field sensor for detecting the response of a rare earth metal oxide casting fragment inclusion through the bending and amplification of the ambient magnetic field at the defect location.

3 Claims, 2 Drawing Sheets

METHOD FOR DETECTION OF RARE EARTH METAL OXIDE INCLUSIONS IN TITANIUM AND OTHER NON-MAGNETIC OR METAL ALLOY CASTINGS

BACKGROUND OF THE INVENTION

1. Field of the Invention

The present invention relates to non-destructive testing equipment and more specifically, a method and apparatus for detecting rare earth metal oxides in the form of mold shell fragments in non-magnetic metal or metal alloy castings.

2. Description Related Art

Titanium castings for the aircraft industry today, as well as for other structurally demanding applications, require quality assurance inspection methods that locate as well as identify flaw or possible flaw indicator areas or conditions within them. Additionally these areas must be identified at some required minimum threshold level of detection with regard to both size and depth location within the part being tested. This demands the test method be sensitive to the particular type of flaw or flaw indicators that are inherent to a specific component, material of that component fabrication, or industrial process used in the parts manufacture such as, titanium and any non-magnetic titanium alloy, or other non-magnetic metal or metal alloy component or assembly formed by various casting processes. The present invention addresses the needs of industry for a more reliable and sensitive method for inspecting titanium, or other non-magnetic metal or alloy castings.

One insidious type of flaw that occurs in investment castings are mold shell fragments. These are inadvertently released from the ceramic shell mold during casting as a result of high thermal stresses and erosion of the mold by the molten metal. The ceramic mold innermost layer (that faces the molten metal) typically contains a rare earth metal oxide(s), for example, erbia. Rare earth oxides are utilized because of their high melting point and chemical compatibility with the reactive titanium melt. Upon release, the mold shell fragments are incorporated into the body of the casting itself, and thereby become inclusion defects. These defects reduce the ability of the part to carry design loads, and must be detected as extensively as possible to avoid compromising the reliability and efficiency of the system that the castings serve. Conventional techniques for detecting such defects have proved inadequate. The present invention hereinafter described addresses the need for an improved method of detection of this type of defect.

a. Prior Nondestructive Testing Methods

A variety of nondestructive methods have been developed to locate and identify castings defects, although these are principally confined to radiography, ultrasonic and eddy current techniques. Radiography is limited by poor contrast between the ceramic inclusions and the titanium alloy itself, since they exhibit similar x-ray penetration densities. This reduces the resolution of radiographic detection to unsatisfactory levels. Large section thicknesses also present difficulty due to high attenuation at available x-ray facilities. Ultrasonic methods suffer partially from the lack of a definitive interface (i.e., a large change in sound speed or wave character) at the defects, and partially from the irregular geometry of many of the structural castings currently being implemented. Eddy current techniques are limited to surface and near-surface defects, and thus of limited utility in the present situation where the inclusions may be deep within the casting body.

3. Prior Art Patents

U.S. Pat. No. 3,065,412 L. A. Rosenthal, Metal Detector

This patent discloses a device for detecting pieces of metal in a non-metallic material. However, this detects the metals by passing the substance between a pole of the magnet and a magnetic backing plate. It senses a change in magnetic flux, using a sensing coil, around the magnet. This system is intended for an assembly line production operation. In contrast, the present invention uses a permanent magnet but does not require a magnetic backing plate between the substance and the magnet. Additionally, the present system utilizes a Hall effect sensor to detect the change in magnetic flux.

U.S. Pat. No. 4,518,919, Ishida, Detecting Device for Detecting a Magnetic Strip Embedded in a Sheet This patent discloses an approach for detecting a magnetic strip embedded in a sheet, such as a currency note. The method disclosed has a permanent magnet located above the conveyor of the currency, and a magnetic resistance detecting element (InSb) located below the currency. When the currency containing the magnetic strip is passed between the magnet and the detecting element, the change in magnetic flux is detected.

U.S. Pat. No. 5,105,151, Takahashi et al., Method and Apparatus for Magnetically Detecting a Carburized Portion of an Article While Discriminating a Non-Carbonized Deteriorated Layer of the Article.

U.S. Pat. No. 5,128,613, Takahashi, Method of Inspecting Magnetic Carborization in a Non-Permeable Material and Probe Therefore Both of these patents disclose a method for detecting a carburized deposit located on the inside wall of a tube. The method of detection utilizes a magnet and a Hall sensor. However, in the first patent two magnets and two sensors are required in order to compare the flux change at the outer surface of the tube with the flux change at the inner surface of the tube. In the second patent, the Hall sensor is positioned between the poles of the magnet and the detecting surface of the Hall sensor is parallel to the direction of the undisturbed field lines. In contrast, the present invention uses a magnet and a Hall sensor to measure a change in the magnetic flux caused by a paramagnetic substance and only one magnet is needed. Additionally, in an embodiment of the present system the Hall sensor is placed directly below and to the side of one of the magnet poles and the detecting surface is perpendicular to the unperturbed field lines.

U.S. Pat. No. 5,432,444, Yasohama et al., Inspection Device Having Coaxial Induction and Exciting Coils Forming a Unitary Coil Unit This patent discloses a method for inspecting an object for defects using an exciting coil for generating an electromagnetic field and an induction coil which are integrally connected to each other so as to induce mutual inductance in the induction coil by the electromagnetic field. This detection method is in contrast to the present method which does not sense a change in mutual inductance.

U.S. Pat. No. 5,589,772, Kugai, Non-Destructive Eddy Current Sensor Having a Squid Magnetic Sensor and Selectively Positionable Magnets This patent discloses a method of detecting defects in objects. However, the detection method is comprised of a SQUID. A SQUID (Superconducting Quantum Interference Device) requires a liquid nitrogen cryogenic support system to provide the low temperatures needed to achieve superconductivity in the detector. The present invention does not require such a costly and complex system.

Further prior art references include:

U.S. Pat. No. 4,814,734, Moran, Search Coil Assembly for Metal Detectors;

U.S. Pat. No. 4,902,997, Moran, Search Coil Assembly for Metal Detectors; and

U.S. Pat. No. 4,943,770, Ashley-Rollman et al., Device for Accurately Detecting the Position of a Feromagnetic Material Inside Biological Tissue.

BRIEF SUMMARY OF THE INVENTION

The present invention incorporates a D.C. magnetic search field coupled with a magnetic field sensor (Hall, squid, magnetoresistive, etc.). The casting is virtually transparent to the magnetic field emanating from the D.C. magnetic field source while the slight but definite paramagnetic response of any rare earth metal oxide casting fragment inclusion will be to bend and amplify the ambient magnetic field at the defect location. The magnetic field is otherwise unaffected by its transit through the metal of the casting except for the dipole field falloff due to distance from the field source (this would be typically a 1/r cube function with r being the radius from the dipole source to the point of the field strength measurement). An embodiment of the invention consists of a Hall magnetic field sensor to which is affixed a permanent magnet such as a high energy density neodymium-iron-boron type. This tandem arrangement of the field source and the magnetic field detector assures that a baseline no-detect location remains invariant. Also, threshold field strength levels provided to the magnetic field sensor instrumentation can be set so as to trigger only when defects of a particular size or depth are detected.

DETAILED DESCRIPTION OF THE INVENTION

Figure 3:
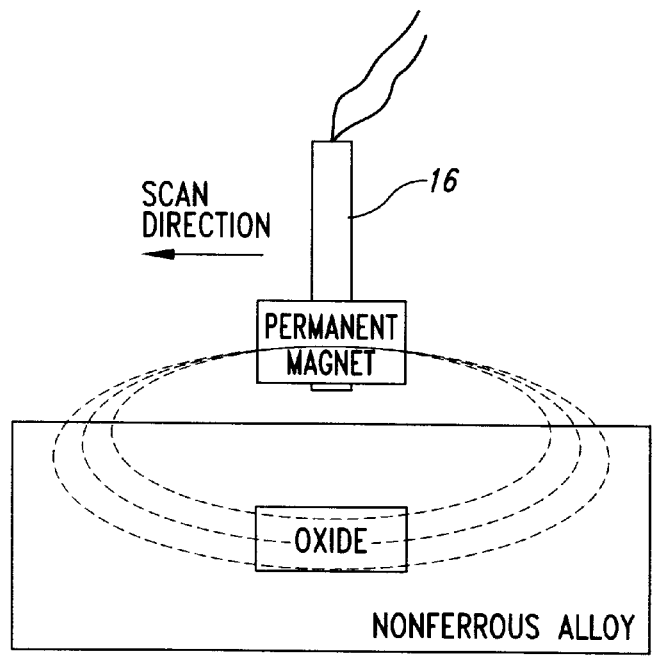
FIG. 3 is a schematic diagram of a prototype apparatus wherein the Hall magnetic sensor is affixed to a permanent magnet in tandem arrangement.

The present method is directed towards overcoming the limitations and drawbacks of other nondestructive evaluation (NDE) methods. The present system incorporates a D.C. magnetic search field (D.C., except for the additional effect of the movement of the detector probe and/or the movement of the casting under inspection), coupled with a magnetic field sensor (Hall, squid or magnetoresistive). The casting (a non-magnetic metal or alloy) is virtually transparent to the magnetic field emanating from the D.C. magnetic field source (such as that provided by a permanent magnet), while the slight, but definite paramagnetic response of any rare earth metal oxide (which includes most rare earth metal oxides, e.g., erbia, gadolinia, dysprosia) casting fragment inclusions will be to bend and amplify the ambient magnetic field at the defect location. The magnetic field is otherwise unaffected by its transit through the metal of the casting except for the dipole field falloff due to distance from the field source (this would be typically a $1/r^3$ function with r being the radius from the dipole source to the point of field strength measurement). The embodiment shown in FIG. 3 consists of a Hall magnetic field sensor to which is affixed a permanent magnet e.g., a high energy density neodymium-iron-boron type. This tandem arrangement of the field source and the magnetic field detector assures that a baseline no-detect condition remains invariant. Also, the no-detect state can be set to a "relative zero" instrumentation reading by nulling out the ambient search field strength, thereby only registering the defect location (i.e., the magnetically perturbed or anomalous response position). Also, threshold field strength levels can be set so as to trigger only when defects of a particular size and/or depth are detected.

Parts to be tested may be inspected, e.g., by an x-y scanner setup or robotic arm arrangement following the surface of a casting with sweeping passes until the required areas have been completely covered. The required sensitivity and resolution, as well as depth of evaluation, can be adjusted by maximizing detector instrument readouts from standards containing intentional rare earth oxide inclusions at various depths with castings of representative thicknesses. This can be optimized by changing the magnetic dipole orientation, dipole length, dipole "pole" strength, orientation of detector probe with respect to the dipole orientation, etc. Furthermore, different magnetic field sensors can provide orders of magnitude differences in sensitivity allowing selection of the most robust detector which is still able to detect the minimum size defect in a particular casting.

Various sensor and magnetic-field-source arrangements can be devised depending on the part geometry and other testing constraints or requirements.

Figure 1:
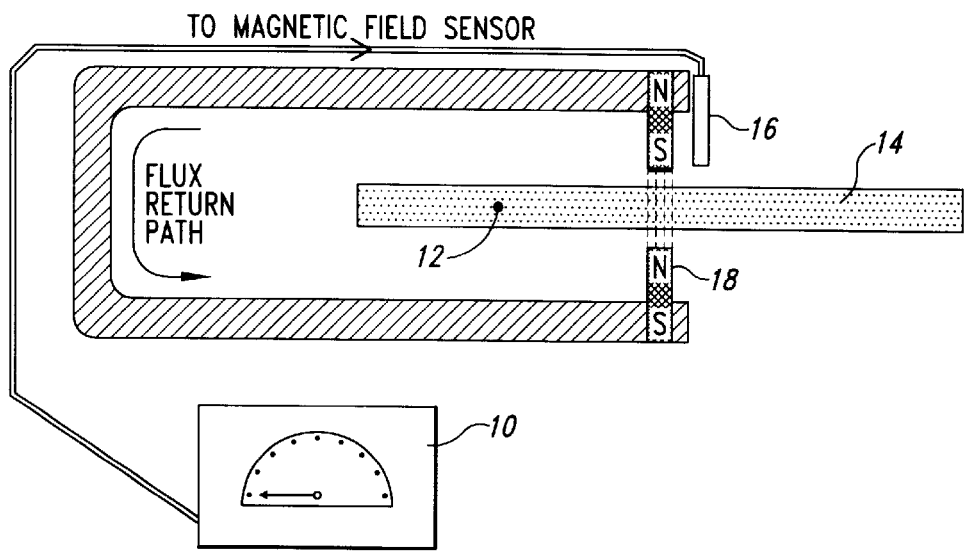
FIG. 1 is a block diagram of a preferred embodiment of the present system showing a side view of the casting part, magnetic field sensor and magnetic field source prior to readout of the presence of a rare earth oxide "inclusion"

As show in FIG. 1, the system for detection of rare earth metal oxide inclusions 12 in a non-magnetic casting part 14 includes magnetic field sensor 16 and magnetic field source 18. Magnetic field sensor instrumentation 10 is coupled to the output of magnetic field sensor 16 and the readout of zero shows that the magnetic field of source magnet 18 is unaffected by the intrusion of non-magnetic material in the form of casting part 14 in the space between magnetic field source 18 and magnetic field sensor 16.

Figure 2:
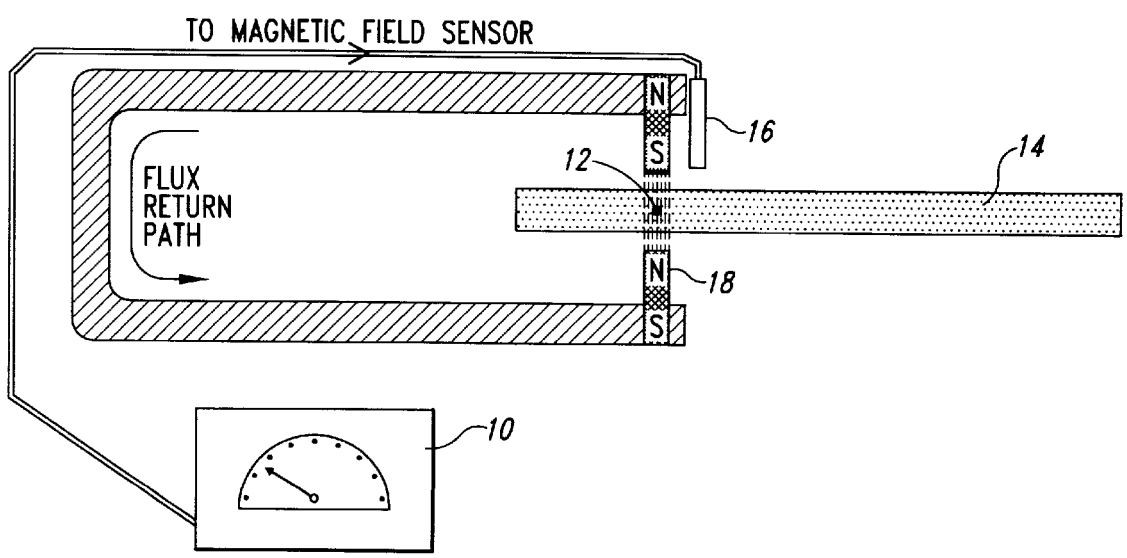
FIG. 2 is a block diagram of the preferred embodiment of the present system shown in FIG. 1 however showing the magnetic field sensor instrumentation readout in the presence of a rare earth oxide inclusion in the casting part.

Turning to FIG. 2, it can be seen that the magnetic field as read out on field sensor instrumentation 10 is perturbed as well as amplified by the magnetic properties of rare earth oxide inclusion 12.

Figure 4:
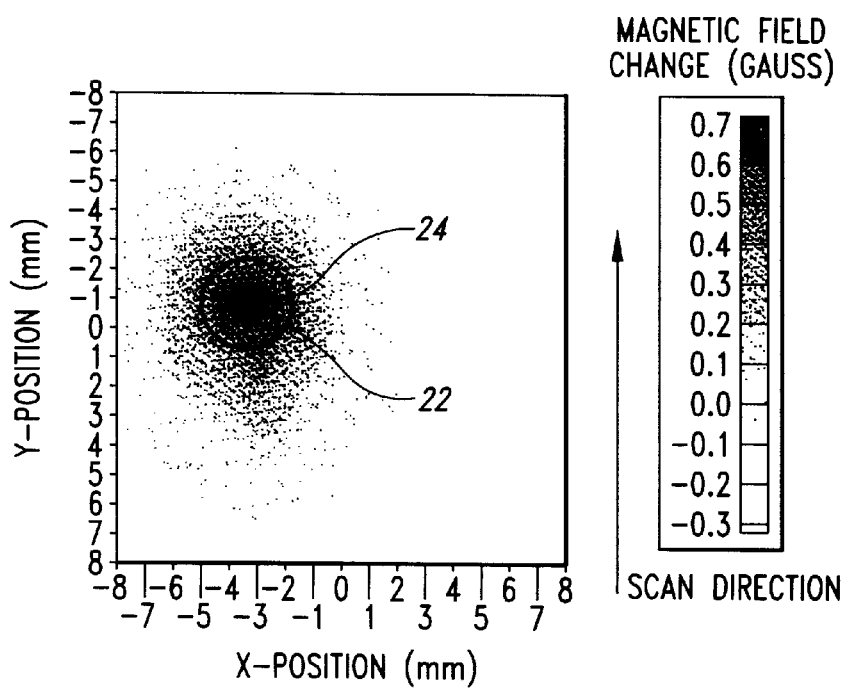
FIG. 4 is a graph illustrative of sample positioning and accompanying scan readout of the magnetic field during scan over a rare earth oxide inclusion.

The principles necessary for successful operation of the present system have been demonstrated in a conservative (non-optimized) prototype. Rare earth oxide particulate 1 mm thick by 3 mm in diameter have been detected at depths up to 6 mm, which includes 5 mm of titanium alloy. The ability to detect a 1 mm diameter by 0.25 mm thick inclusion within 3–6 mm of the surface would be a significant benefit. Loads are typically highest at the surface, so this is the region of greatest concern for detectability. An example output from the device is shown in FIG. 4 with the oxide region 24 within sample region 22.

The principle of operation of the present invention does not rely on, nor is it limited by, the size of the titanium casting being inspected. The sensitivity depends primarily on the applied field character, the magnetic field sensor (or sensor array), and the arrangement of the source and detector relative to the defect. Smaller defects at greater depths can be detected by varying these parameters. In addition, by analyzing the vector components of the magnetic response it should be able to determine the depth of the defect as well as the x-y location. The combination of increased sensitivity to difficult-to-locate defects plus depth locating indicates a significant advance over currently available technologies.

The preceding and further advantages will appear to those skilled in the art upon a reading of the foregoing specification.

While the preferred embodiments of the invention have been illustrated and described, variations will be apparent to those skilled in the art. Accordingly, the invention is not to be limited to the specific embodiments illustrated and described, and the true scope of the invention is to be determined by reference to the following claims.

What is claimed is:

1. A method for detecting a rare earth metal oxide inclusion in a non-magnetic casting part comprising the steps of:

passing a magnetic field through a non-magnetic casting having a rare earth metal oxide inclusion; and detecting the paramagnetic response of said rare earth metal oxide inclusion by measurement of the amplified ambient magnetic field resulting from said rare earth metal oxide inclusion.

2. An apparatus for sensing the paramagnetic response of a rare earth metal oxide casting inclusion in a non-magnetic casting comprising in combination:

a Hall magnetic field sensor;

permanent magnets;

said Hall magnetic field sensor and the magnetic field source are fixed relative to one another with respect to distance and orientation for providing a baseline magnetic field amplitude in the absence of rare earth oxide inclusion.

3. In combination in a method for manufacturing non-magnetic metal castings:

providing a shell mold having a face coat containing a rare earth metal oxide;

casting the molten non-magnetic metal in said shell mold thereby causing mold face coat fragments to be introduced into the casting upon release of the casting; and utilizing paramagnetic response of said mold face coat fragments to detect defects in said casting.

* * * * *